(12) United States Patent
Roget et al.

(10) Patent No.: US 7,998,726 B2
(45) Date of Patent: Aug. 16, 2011

(54) METHOD FOR FIXING A PROTEIN ON A PYRROLE-BASED POLYMER AND USE THEREOF FOR MAKING A SENSOR

(75) Inventors: Andre Roget, Brie et Angonnes (FR); Thierry Livache, Haute-Jarrie (FR); Yves Levy, Malakoff (FR)

(73) Assignees: Commissariat a l'Energie Atomique, Paris (FR); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 10/533,950

(22) PCT Filed: Nov. 20, 2003

(86) PCT No.: PCT/FR03/50127
§ 371 (c)(1), (2), (4) Date: May 4, 2005

(87) PCT Pub. No.: WO2004/048972
PCT Pub. Date: Jun. 10, 2004

(65) Prior Publication Data
US 2006/0035208 A1   Feb. 16, 2006

(30) Foreign Application Priority Data
Nov. 21, 2002 (FR) ...................................... 02 14580

(51) Int. Cl.
*C12M 1/34* (2006.01)
*G01N 33/53* (2006.01)
*G01N 33/551* (2006.01)
*G01N 33/544* (2006.01)
*G01N 33/547* (2006.01)

(52) U.S. Cl. ...... 435/287.2; 435/7.1; 436/524; 436/528; 436/532

(58) Field of Classification Search ............... 435/287.2, 435/970; 436/6, 528, 544, 823; 530/812, 530/405; 548/400, 546
See application file for complete search history.

(56) References Cited

U.S. PATENT DOCUMENTS
| | | | |
|---|---|---|---|
| 6,160,103 A | 12/2000 | Marchand et al. | |
| 6,803,228 B1 * | 10/2004 | Caillat et al. | 435/287.2 |
| 2003/0207400 A1 * | 11/2003 | Bianchi et al. | 435/69.1 |
| 2006/0013850 A1 * | 1/2006 | Domb | 424/422 |

FOREIGN PATENT DOCUMENTS
| | | |
|---|---|---|
| FR | A-2 750 136 | 12/1997 |
| WO | 00/36145 | 6/2000 |

OTHER PUBLICATIONS

Livache et al. "Electroconducting polymers for the construction of DNA or peptide arrays on silicon chips", Biosensors & Bioelectronics, vol. 13, pp. 629-634, XP002249768 1998.
Bidan et al. "Conducting Polymers as a link between biomolecules and microelectronics", Synthetic Metals, vol. 102, pp. 1363-1365, XP002114817 1999.
Livache et al. "Polypyrrole DNA Chip on a Silicon Device: Example of Hepatitis C Virus Genotyping", Analytical Biochemistry, vol. 255, pp. 188-194, XP02114813 1998.
Wolowacz et al. "Covalent Electropolymerization of Glucose Oxidase in Polypyrrole", Anal. Chem., vol. 64, pp. 1541-1545, XP002030300 1992.
Yon-Hin et al. "Covalent Electropolymerization of Glucose Oxidase in Polypyrrole. Evaluation of Methods of Pyrrole Attachment to Glucose Oxidase on the Performance of Electropolymerized Glucose Sensors", Anal. Chem., vol. 65, pp. 2067-2071, XP000885233 1993.
Foulds et al. "Enzyme Entrapment in Electrically Conducting Polymers", J. Chem. Soc., Faraday Trans. 1. vol. 82, pp. 1259-1264 1986.
Guedon et al. "Characterization and Optimization of a Real-Time, Parallel, Label-Free, Polypyrrole-Based DNA Sensor by Surface Plasmon Resonance Imaging", Anal. Chem., vol. 72, pp. 6003-6009 2000.
Carlsson et al. "Protein Thiolation and Reversible Protein-Protein Conjugation", Biochem. J., vol. 173, pp. 723-737 1978.
Sadik et al. "Monitoring the specific adsorption of proteins using the electrochemical quartz crystal microbalance electrodes", Talanta, vol. 55, pp. 929-941 2001.
Schuhmann. "Conducting Polymer Based Amperometric Enzyme Electrodes", Mikrochim. Acta., vol. 121, pp. 1-29 1995.
MacBeath et al. "Printing Proteins as Microarrays for High-Throughput Function Determination", Science, vol. 289, pp. 1760-1763 2000.

* cited by examiner

Primary Examiner — Shafiqul Haq
(74) Attorney, Agent, or Firm — Oblon, Spivak, McClelland, Maier & Neustadt, L.L.P.

(57) ABSTRACT

The aim of the present invention is to provide a method for attaching a protein to a conductive polymer, that can be used in particular for producing a sensor or a multisensor, for example a biochip.
This aim, and also others, are achieved, in accordance with the invention, by means of a method for attaching a protein to a pyrrole polymer, comprising the following steps:
coupling of the protein to be attached with pyrrole so as to obtain a first solution of a protein-pyrrole coupling compound,
preparation of a second solution of pyrrole not containing the protein,
mixing of said first solution with said second solution so as to obtain an electropolymerization solution,
electropolymerization of the pyrrole and of the protein coupled to the pyrrole on a conductive support using said electropolymerization solution.

17 Claims, 8 Drawing Sheets

(d) Control, IF = 80

METHOD FOR FIXING A PROTEIN ON A PYRROLE-BASED POLYMER AND USE THEREOF FOR MAKING A SENSOR

TECHNICAL FIELD

The present invention relates to a method for attaching a protein to a pyrrole-based polymer, and also to the use of this method for producing sensors, in particular multisensors, for example biochips.

The techniques of the prior art have not, or only with great difficulty, been able to immobilize proteins on a conductive polymer without modifying their activity, in particular to immobilize two different proteins separately, in particular for the production of sensors, especially in the biochip field.

In fact, proteins, for example enzymes, antibodies, receptors and certain antigens, have recognition sites for target molecules or sites that enable them to be recognized by other molecules. These sites are responsible for their activity or activities. For example, an enzyme has a specific site for its substrate, an antibody has a specific epitope allowing recognition by its corresponding antigen, and an antigen has a recognition site specific for the epitope that it targets. These sites are generally formed due to folding of the protein on itself in space, which folding can be stabilized by disulphide, ionic, hydrogen and hydrophobic bonds. This folding and, as a result, the sites that it forms, can therefore be readily destabilized by means of a simple constraint applied to the protein, by steric hindrance, or by a change in ionic strength, in pH or in temperature of the medium. In addition, these sites have reactive functions such as $-NH_2$, $-OH$, $-COOH$ or $-SH$ functions that are capable of reacting with the reagents or the monomers used during the attachment of the protein to the conductive polymer, and can therefore be damaged, blocked or hindered.

The methods used to attach a protein having such a site to a surface in order to exploit this site must therefore, as far as possible, preserve this site so that the sensor produced may perform its function, providing sample analysis results that are as precise, sensitive and reproducible as possible.

STATE OF THE PRIOR ART

In the techniques known to those skilled in the art, the immobilization of proteins to a conductive polymer can make use of four different techniques. These four techniques are entrapment, post-functionalization, non-covalent immobilization of proteins, and covalent immobilization of proteins. These techniques are represented diagrammatically in the attached FIGS. 1 to 4. In these figures, "P" and "Pa" represent, respectively, the protein and the activated protein, "m" and "ma" represent, respectively, a monomer and an activated monomer of the polymer, "P-m" represents a protein-monomer coupling compound, and "M" and "Ma" represent, respectively, the polymer and the activated polymer.

In the entrapment technique, the monomer is subjected to polymerization in the presence of the protein. In forming, the polymer traps this protein in its network. This technique is described, for example, by Foulds and Lowe in *J. Chem. Soc., Faraday Trans.* 1986, 82, 1259-1264, and is illustrated in the attached FIG. 1. It is advantageous since it makes it possible not to modify the protein before it is immobilized and therefore, in principle, to obtain better conservation of its activity. This method was reiterated more recently by O A Sadik et al., *Talanta* 2001, 55: 929-941.

Unfortunately, this method does not make it possible to target via the current only the protein onto a selected electrode, neither does it make it possible to carry out several deposits of different proteins without contamination of the deposits from one deposit to another, due to the mechanism of immobilization by entrapment. In fact, in this technique, proteins may be partially entrapped and released during polymerization of subsequent deposits, and may therefore contaminate the latter. In addition, the immobilization time is quite long and contaminations are possible between the deposits, which makes it difficult to produce multisensors, and as a result it is used to produce monosensors.

Moreover, it is a technique consisting of immobilization in the mass of the polymer, which results in the following various drawbacks:

a decrease in, or even an elimination of, access to the active site of the protein, due to the fact that the protein is caged in a medium with a polarity that is very different to that of the medium studied, for example a sample to be analyzed, the recognition between the protein and its target is disturbed in addition to the abovementioned steric hindrance, if the recognition between the protein and its target requires or induces changing the structure of the protein, this change may be hindered by the rigidity of the polymer, and detection of the interaction of the protein with its target can only be carried out in the mass, which prohibits the most common optical methods of analysis. On the other hand, it is very suitable for electrochemical detection, for example in the form of biosensors.

This technique requires, in addition, quite a large thickness of polymer in order to cage the protein. This has the following drawbacks:

the amount of protein used must be greater than a simple deposit, and the exposure to the electric current must be longer; according to the document Sadik et al., mentioned above, the charge density is of the order of 2 $nC/mm^2$ (i.e. a polymer thickness of approximately 500 nm).

Yet another drawback is the fact that if the entrapment of the protein is not perfect, this results in a loss of the amount of protein during successive polymerizations or uses or during storage, with a decreasing sensitivity of the sensor and contamination in the case of a multisensor.

Figure 1:
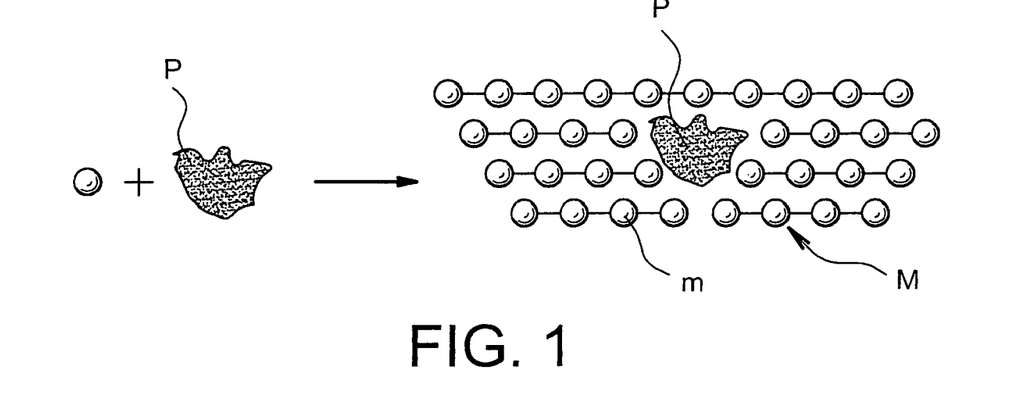
FIGS. 1 to 4 represent diagrammatically the techniques of the prior art, and the results that they produce (on the right).
Figure 2:
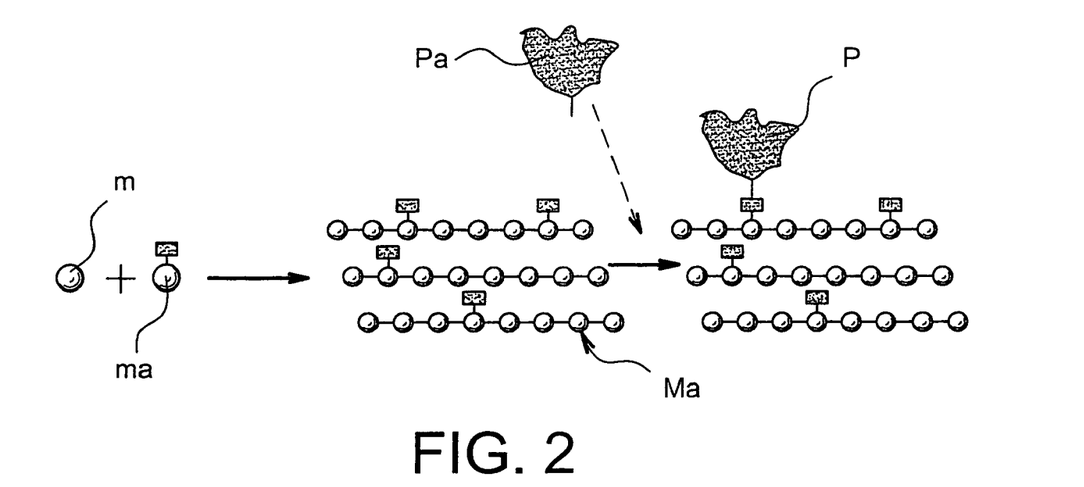

The post-functionalization technique is represented diagrammatically in the attached FIG. 2. It involves grafting proteins that have been activated, either with activated esters or with maleimides mainly, onto supports that have been functionalized with $NH_2$ or SH groups or, conversely, grafting proteins that may or may not have been functionalized using the $NH_2$ groups from the lysines or the SH groups from the cysteines of these proteins, onto supports that have been activated with activated esters or maleimides, respectively. This method is described, for example, by W. Schuhman in *Mikrochim. Acta* 121, 1-29 (1995). It enables surface grafting which induces surface detection.

This grafting is, unfortunately, not easy to control due to the weak reactivity of the functions involved. In addition, it is suitable for the production of monosensors, and allows only with great difficulty the production of multisensors. In fact, if it is desired to produce a multisensor containing several spots, since the reactivity is weak in this technique, all the functions of the first spot, for example, have not reacted when the second protein is attached to the second spot, and there is therefore contamination of the second protein on the first spot. In order to avoid this, the protein must be introduced only onto the deposit selected. This can be difficult to miniaturize since, although it is effectively possible to deposit microdrops in a localized manner, their rate of evaporation is very rapid and the reaction is difficult to control. In this case, there is no advantage to using a support of the conductive polymer type since the targeting must be carried out mechanically, for example using an inkjet system. Such technologies are used to produce protein chips on glass slides, as is described in G. MacBeath *Science,* 8 Sep. 2000, Vol. 289, 1760-1763.

Figure 3:
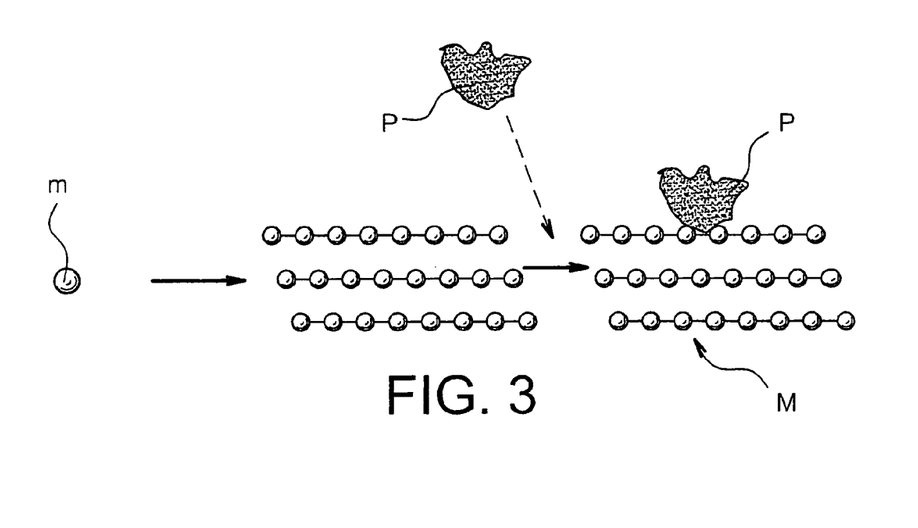
Figure 4:
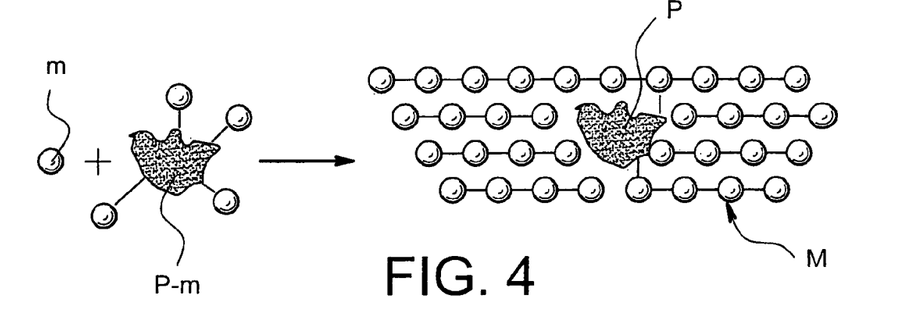
Figure 5:
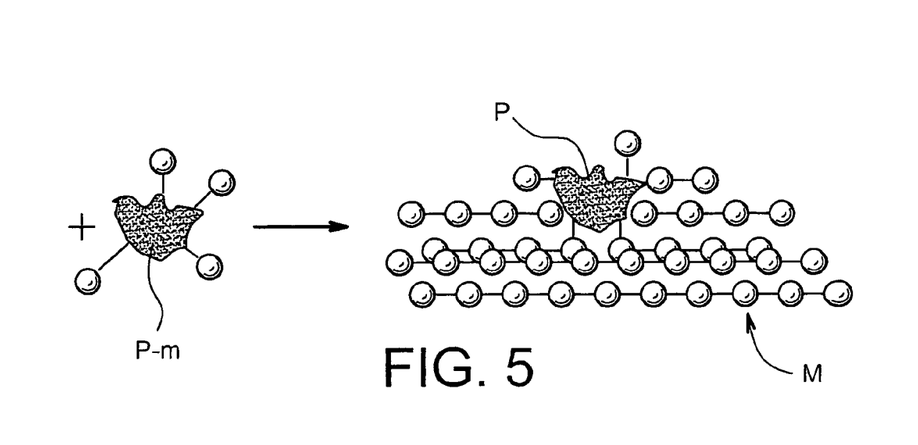
FIG. 5 represents diagrammatically the method of the present invention and the result that it produces.

The technique of non-covalent immobilization of proteins without prior chemical modification of these proteins is represented in the attached FIG. 3. In this technique, the biotin-avidin system is used. The document Farmakovsky et al., WO 00/11473, describes this technique. There is formation of a conductive polymer with proteins that are more or less well immobilized by adsorption.

The fact that the attachment to the support is so weak is certainly not favourable to the storage of this electrode and even less so to the production of a multisensor.

The fourth technique is covalent entrapment. It is represented diagrammatically in the attached FIG. 4. This technique has been described in the prior art by Wolowacz S. E., Yon Hin B. F. Y. and Lowe C. R. *Anal. Chem.* 1992, 64, 1541-1545. The author prepared an enzyme, glucose oxidase, in such a way as to conjugate it to pyrrole and subjected it to copolymerization with pyrrole. The pyrrole grafted onto the enzyme electropolymerizes and immobilizes the enzyme in a sort of polypyrrole coating.

Unfortunately, the enzyme is entrapped in the pyrrole, which limits its accessibility with respect to the outside medium and the burial of its active site. This accessibility can, in certain cases, be conserved, but only for very small molecules, such as glucose in the publication mentioned above, capable of penetrating into the mesh of the polypyrrole network. In fact, the abovementioned drawbacks of the entrapment technique mentioned above are retained, only the stability is increased.

There exists therefore a real need for a method for attaching a protein to a conductive polymer that does not have the drawbacks, limitations, deficiencies and disadvantages of the methods of the prior art.

In addition, it must be possible for this method to be used for producing a sensor, in particular for producing a multisensor, such that it does not have the drawbacks, limitations, deficiencies and disadvantages of the methods and of the sensors of the prior art.

DISCLOSURE OF THE INVENTION

The aim of the present invention is precisely to provide a method for attaching a protein to a conductive polymer, that can be used in particular for producing a monosensor or a multisensor, that satisfies, inter alia, the needs indicated above.

This aim, and also others, are achieved, in accordance with the invention, through a method for attaching a protein to a conductive support by means of a pyrrole polymer, comprising the following steps:
  coupling of the protein to be attached with a pyrrole monomer so as to obtain a first solution of a protein-pyrrole coupling compound,
  preparation of a second solution of the pyrrole monomer not coupled to the protein,
  mixing of said first solution with said second solution so as to obtain an electropolymerization solution,
  electropolymerization of the pyrrole and of the protein coupled to the pyrrole on at least one given area of the conductive support using said electropolymerization solution, said electropolymerization being carried out by delivering onto said area an amount of current of 1 to 500 microcoulomb/mm$^2$ (1 to 500 µC/mm$^2$).

According to the invention, the term "pyrrole monomer" is intended to mean a monomer of pyrrole or a polymerizable derivative of pyrrole. The pyrrole monomers that can be used in the present invention are those that are known to those skilled in the art in methods for producing biochips. As a derivative of pyrrole, mention may be made, for example, of methyl pyrrole, or substituted or unsubstituted pyrrole dimers.

According to the invention, one or more proteins can be attached to a support by means of the method of the invention. Those skilled in the art will, in light of the present description, know how to prepare the electropolymerization solution according to their needs, with one or more proteins, each coupled to the pyrrole monomer chosen, each deposited onto one or more areas of the support.

According to the invention, the expression "area of the support" is also intended to mean "block", for example a block of a biochip support. According to the invention, the electropolymerization can be carried out simultaneously on several areas or blocks of the biochip produced, or successively on several areas or blocks of the biochip produced, for example with various proteins. The choice of the number of areas or blocks will depend in particular on the desired resolution of the biosensor, and on the number of simultaneous analyses that can be carried out with the desired biosensor. The number of areas or blocks can be determined as for the biochips known to those skilled in the art. For the purpose of the present invention, the conductive support can therefore advantageously be a biochip support with one or more block(s). The method of the present invention therefore makes it possible to produce, as desired, monosensors or multisensors.

The present invention makes it possible, surprisingly, to conserve the activity of the protein attached to or immobilized on the polymer, for example the properties of recognition of a protein with respect to large molecules, for example of an antigen with respect to its corresponding antibodies.

This was not possible with the techniques of the prior art since the pyrrole reacted with most of the amine functions of the proteins. Now, by means of the method of the present invention, entirely unexpectedly, the inventors have generated polypyrrole-protein deposits in which the activity of the protein, immobilized in or on a thin layer of polymer, is conserved. In addition, the present invention makes it possible to construct an extremely thin film that further preserves the activity of the protein.

In fact, the inventors have prepared various pyrroles that they have reacted with proteins, as is illustrated in the examples below. These conjugated proteins are subsequently immobilized by electropolymerization with pyrrole. Be that as it may, and despite the lack of knowledge of the phenomenon in question, they have, by means of this method, been able to target antigenic proteins onto a conductive substrate and to have them recognized by a specific antibody.

The inventors have studied this recognition by fluorescence, which has enabled them to verify that the protein is indeed immobilized at the surface, since the fluorescence can only be detected outside the polypyrrole matrix. This has made it possible to validate the immobilization by electrocopolymerization in accordance with the present invention and also the recognition by another molecule that can be as bulky as an antibody.

The inventors have also carried out a surface plasmon resonance (SPR) imaging study that makes it possible to go further in terms of analysis due to the fact that it is a real-time analytical method. These kinetic studies make it possible to obtain a better evaluation of the conservation of the activity by virtue of the method of the present invention. Moreover, this analytical method is well known for detecting only the biological interactions that take place at a very small distance from the layer of gold, as is described in P. Guedon et al. *Anal.*

According to the invention, the pyrrole activation can be carried out, for example, by means of N-hydroxysulphosuccinimide or of maleimide.

According to the invention, the protein-pyrrole coupling compound can advantageously be chosen from the following compounds:

*Chem.* (2000), 72, (24), 6003-6009. This distance is often less than 50 nm.

It ensues from these two experiments that the interaction takes place both at the surface of the polymer (fluorescence) and very close to the gold. This means that the polymer must be extremely thin, which is the case by means of the method of the invention.

Thus, according to the invention, the electropolymerization is carried out by limiting the amount of current delivered during the polymerization. As a result, better results have thus been obtained. It is possible that the amount of current in accordance with the present invention limits the length of the polypyrrole chains. This would therefore limit the loss of activity of the protein when it is immobilized. Another possibility could be that the polymerization takes place in the immediate vicinity of the electrode, which would have the effect of minimizing the polymerization of the pyrrole on the part of the protein furthest from this electrode, and therefore of conserving its recognition activity. More probably, the inventors think that there is screening by the protein, that is less conductive than the reaction medium, with respect to the electric field.

Thus, the electropolymerization is carried out by means of the electrochemical electropolymerization method of the present invention, by delivering onto said area an amount of current of 1 to 500 µC/mm², preferably of 5 to 100 µC/mm² (the amount of current can be delivered by electric polarization of said area). As a result of this, there is formation of a polymer having very advantageously a thickness that may be less than 10 nm. By way of example, this polymerization can be carried out according to the invention by means of an electric pulse, applied to said area, of 1 V/ECS for 500 ms.

According to the invention, the coupling of the protein to be attached with pyrrole can be carried out by activation of the pyrrole followed by coupling of the activated pyrrole to the protein to be attached. The activated pyrrole may, for example, be an activated ester of pyrrole that is reactive on the amine functions of the lysines, or a maleimide pyrrole that is reactive on the —SH functions of the cysteines. These examples are not limiting, and those skilled in the art will know how to adapt the method of the invention with other pyrrole activations.

According to a particular embodiment of the present invention, several proteins can be attached to the pyrrole polymer, successively and on different and given areas of the conductive support. For example, two proteins can be attached to the pyrrole polymer, successively and on two different given areas of the conductive support.

This particular embodiment of the invention consists, in other words, of a method for producing a multisensor containing at least two different proteins, at least part of which is located at the conductive polymer/reaction medium interface, this multisensor being obtained by copolymerization of a polymerizable monomer and of proteins onto which it is possible to graft an identical or different monomer capable of copolymerizing.

Thus, the method of the present invention can advantageously be used for producing a sensor or a multisensor, for example a biochip, since it makes it possible to do away with the abovementioned drawbacks of the prior art. The sensors produced provide precise, sensitive and reproducible sample analysis results.

According to the invention, the protein can be chosen, for example, from the group consisting of an enzyme, an antibody, an antigen, a hormone, a receptor, etc., which gives the present invention a broad field of application.

Other advantages will become further apparent to those skilled in the art on reading the examples that follow, given in order to illustrate the application, and not to limit it, with reference to the attached figures.

BRIEF DESCRIPTION OF THE FIGURES

FIGS. 7*a*), *b*), *c*) and *d*) represent micrographs of the measurement of the fluorescence intensities of various streptavidin-biotin conjugates.

FIGS. 8*a*) and 8*b*) represent, respectively, a micrograph of the measurement of fluorescence intensities of various streptavidin-biotin conjugates, and a diagram of the spots obtained on the micrograph.

EXAMPLES

Example 1

Preparation of Activated Esters of Pyrrole

A) Synthesis of Sulpho-N-Hydroxysulphosuccinimide (Sulpho-NHS) Pyrrole

The following are introduced into a 25 ml round-bottomed flask, in order: 11-(1-pyrrolyl)undecan-1-oic acid (2 mmol; 503 mg), of N-hydroxysulphosuccinimide (2 mmol; 434 mg) and dicyclohexylcarbodiimide (DCC) (2.4 mmol; 495 mg). 10 ml of dimethylformamide (DMF) are subsequently added. A cloudy mixture is obtained, which is subjected to magnetic stirring overnight.

The reaction mixture is subsequently filtered under vacuum. The dicyclohexylurea (DCU) precipitate, formed during the reaction, is eliminated. The filtrate containing the product is evaporated in a rotary evaporator.

The product obtained is taken up in 25 ml of water. This solution is washed with three times 50 ml of dichloromethane, in order to eliminate the residual DCC. The water is subsequently eliminated in a Speedvac (registered trademark) overnight.

The yield of the reaction is 65%.

B) Synthesis of Maleimide Pyrrole

Preparation of the Activated Ester of Maleimide

Maleimide acid (3.7 g; 17.5 mmol), NHS (2 g; 17.5 mmol), DCC (3.6 g; 17.5 mmol) and DMF (90 ml) are subjected to magnetic stirring overnight. The chemical reaction for coupling of the maleimide with the pyrrole is represented below.

The mixture obtained is filtered in order to eliminate the DCU. The filtrate is subsequently concentrated.

A white powder is obtained. The product was used as it was, without further purification.

Coupling of the maleimide with the pyrrole:

X being a group —$CH_2$, n being an integer such that $1 \leq n \leq 20$.

For example, $[X]_n$ may be such as the maleimide pyrrole which is defined below in points i), ii) and iii).

i) Maleimide-[2]-pyrrole:

The mixture of activated ester of maleimide (924 mg; 3 mmol), of N-aminoethylpyrrole (330 mg; 3 mmol) and of 15 ml of DMF is stirred overnight. Thin layer chromatography (TLC) makes it possible to verify that the reaction is complete.

After evaporation of the DMF, the product is purified by chromatography on a silica column. The elution is begun with pure dichloromethane, and is continued with an increasing gradient of MeOH (elution of the product: 98%-2%).

The mass obtained is 0.4 g. The final yield of the reaction is therefore 45%.

ii) Mleimide-[6]-pyrrole:

The reaction is carried out with magnetic stirring overnight after mixing, in DMF (15 ml), of the activated ester of maleimide (0.924 g; 3 mmol) and of N-aminohexylpyrrole (0.498 g; 3 mmol). The elution on the silica column is carried out with a $CH_2Cl_2$/MeOH (97%-3%) mixture.

A 46.4% yield for this reaction is obtained with a mass of 0.5 g. The product obtained is a brown liquid.

iii) Pyrrole-[13]-maleimide:

Since the protocol is identical to that above, activated ester of maleimide (1.14 g; 3.70 mmol) and pyrrole-[13]-amine (1 g; 3.70 mmol) are mixed in 20 ml of DMF. The elution on a silica column is carried out with a $CH_2Cl_2$/MeOH (97%-3%) mixture. The mass of the product obtained (brown liquid) is 1 g, i.e. a final yield of 58%.

Example 2

Couplings on Streptavidin

A) Coupling on Streptavidin Using NHS-Pyrrole

Two types of NHS-pyrroles produced as in Example 1 above are used in comparison: NHS pyrrolyl caproate and sulpho-NHS pyrrolyl undecanoate.

A procedure is carried out with an initial molar ratio (IMR) equal to 40, i.e. 40 NHS-pyrrole per protein; thus, 5.55 nmol of streptavidin taken up in 300 µl of coupling buffer are added to 222 nmol of NHS-pyrrole (148 µl of a solution of 1.5 mM NHS-pyrrole), whatever it may be. The coupling reaction is left for 2 hours.

Three reactions are carried out in parallel:
the first uses the NHS pyrrolyl caproate,
the second uses the sulpho-NHS pyrrolyl undecanoate, and
the last is a control containing only streptavidin alone, in solution in coupling buffer.

The purification after reaction is carried out using Nalgene 30K filters (brand name), according to the manufacturer's protocol.

375 µl of each sample are each deposited onto different filters, and centrifuged for 15 minutes at 8000 rpm. Each filter is then rinsed three times with 200 µl of "spotting" buffer; a centrifugation for 15 to 20 minutes is necessary between each wash.

At the end, three fractions of 50 µl are recovered:
streptavidin-NHS pyrrolyl caproate
streptavidin-sulpho-NHS pyrrolyl undecanoate
streptavidin alone B) Coupling of the Maleimide-Pyrroles to Streptavidin Since streptavidin does not have any SH functions, they are created by means of a bifunctional reagent, N-succinimidyl-3-[2-pyridyldithio]propionate (SPDP), which reacts with the amine functions of the protein. The SH groups of this reagent are subsequently released by means of dithiothreitol, hence the advantage of using these reagents. This technique is described, for example, in Carlson, T., Drevin, M. and Axen, R. (1978) *Biochem. J.* 173, 723-727.

The three maleimides produced as in Example 1 above are therefore:
ethyl maleimide-pyrrole
trioxatridecanoyl maleimide
hexyl maleimide-pyrrole.

a) Creation of the Free SH Functions 4.2 nmol of streptavidin are reacted with 150 nmol of SPDP. The reaction is left for 40 minutes. The mixture is then filtered using Nalgene 30K filters, and rinsed three times with 100 µl of 50 mM sodium acetate buffer, pH 4.5.

62.5 nmol of dithiothreitol are subsequently added to the streptavidin-SPDP (SA-SPDP) solution obtained. The reaction is left for 40 minutes. Filtration is again carried out in the same manner as previously, the rinsing being carried out with a PBS buffer solution in order to recover the streptavidin (SA) with accessible free thiol functions (SA-SH), in a volume of 150 µl.

The sample obtained is subsequently separated into three fractions of 50 µl, to which 85 nmol of maleimide-pyrrole are added.

b) In the Case of Ethyl Maleimide-Pyrrole (MW=303 g/mol)

SA-SH is mixed with a 25 nmol/µl solution of maleimide-pyrrole (3.4 µl; 85 nmol) prepared by taking up 2 mg of maleimide-pyrrole in 200 µl of DMF. The reaction lasts 30 minutes.

c) In the Case of Trioxatridecanoyl Maleimide (MW=463 g/mol)

The reaction is carried out in the same way as that above, adding SA-SH to a 39 nmol/µl solution of maleimide-pyrrole (2.2 µl; 85 nmol) prepared by taking up 1 mg of maleimide-pyrrole in 50 µl of DMF. The reaction is left for 30 minutes.

d) In the Case of Hexyl Maleimide-Pyrrole (MW=359 g/mol)

The SA-SH is mixed with a 57.5 nmol/µl solution of maleimide-pyrrole (1.5 µl; 85 nmol) prepared by taking up 3 mg of maleimide-pyrrole in 200 µl of DMF. The reaction is carried out for half an hour.

After the reaction, the various reaction mixtures and also the control solution (streptavidin alone, without added reagent) are centrifuged through Nalgene 30K filters and rinsed with spotting buffer. Finally, all the samples are brought to a final volume of 50 µl, by making the volume up with spotting buffer (50 nM sodium phosphate buffer, pH 7).

Example 3

Electrochemical Synthesis of Polypyrroles ("Spotting"): Electropolymerization

Figure 6:
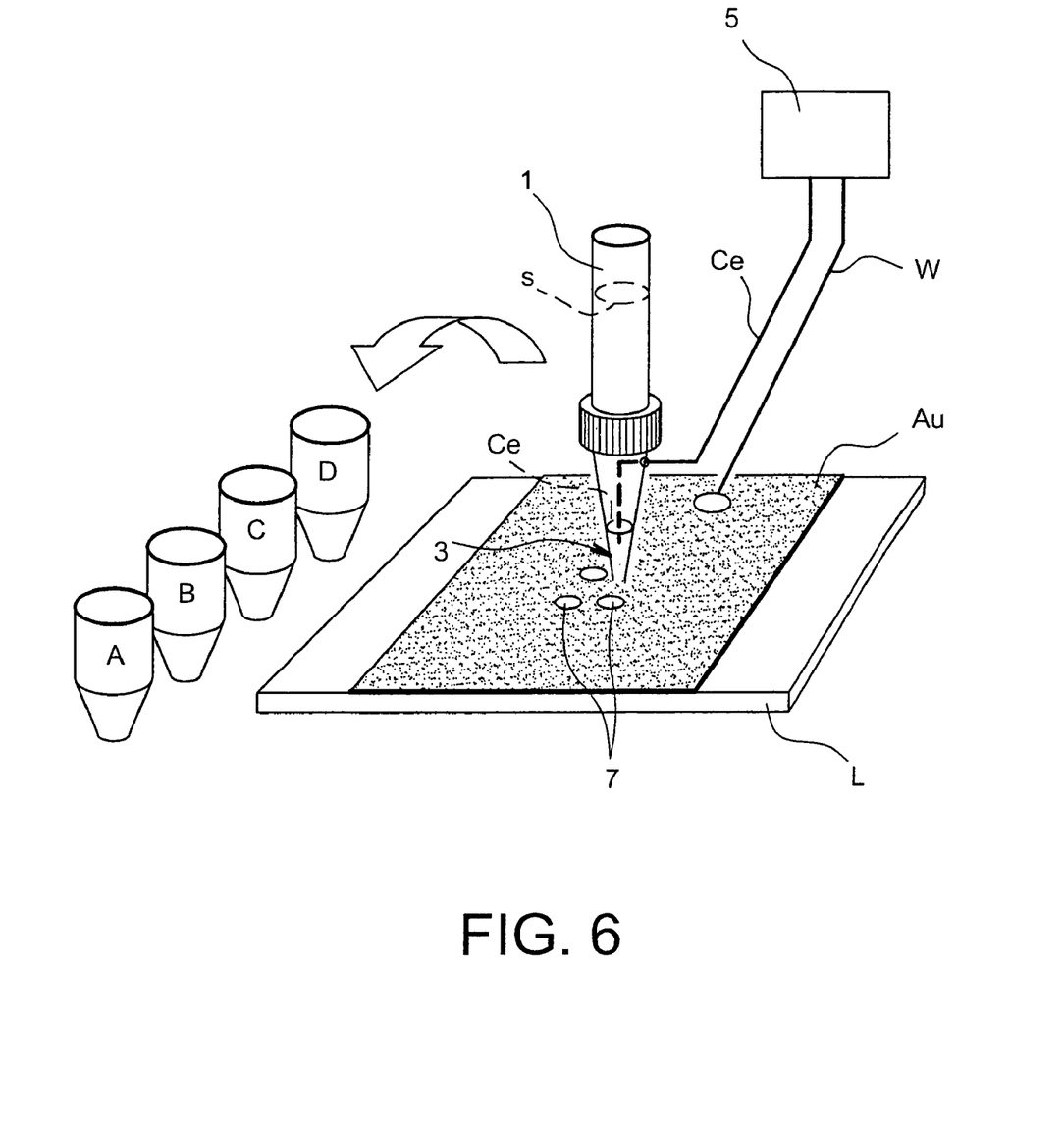
FIG. 6 represents diagrammatically the device used for carrying out the method of the invention.

The reaction is carried out using the "spotting" assembly represented in the attached FIG. 6, which is described, moreover, in detail in the document P. Guedon et al., mentioned above. In this figure, "A" and "B" correspond to streptavidin coupled to polypyrrole via, respectively, the NHS caproate and the sulpho-NHS undecanoate; "C", corresponds to streptavidin coupled to pyrrole via the hexyl maleimide, and "D" corresponds to streptavidin alone. "L" represents a glass slide; "Au" a layer of gold deposited on this glass slide (the combination is hereinafter called "gold slide"); "s" the electropolymerization solution; and "W" the working electrode. Reference 1 indicates a pipette; reference 3 the tip of the pipette; and reference 7 polypyrrole spots deposited onto the gold layer.

As is represented in this figure, the gold slide on which the electropolymerization is carried out serves as a working electrode (W), and a platinum wire placed in the depositing pipette tip serves as a counterelectrode (Ce). This electrochemical system is connected to the potentiostat 5.

The copolymerization is carried out with 20 µl of a solution containing 5 µl of the SA-maleimide-pyrrole solution, chosen from those produced in the previous example, and 15 µl of the spotting solution comprising 50 mM phosphate buffer, with a pH of 7, and 20 mM pyrrole.

The film is synthesized on the gold layer subsequent to an electric pulse that lasts 500 ms and rises to 2.4 V (i.e. approximately 0.9 V/ECS).

The various spots are all produced in the same way, the pipette tip being rinsed with water between each polymerization.

Example 4

Phase Consisting of Detection of the Proteins Grafted onto the Spots

After the electrochemical synthesis of Example 3, the area containing the spots is delimited by a hydrophobic barrier produced using an adhesive felt pen. The spots are subsequently washed twice with 1 ml of rinsing buffer. They are then blocked with 100 µl of blocking buffer, in order to prevent the nonspecific attachment of proteins, which are deposited within the hydrophobic area previously delimited. After a second rinsing identical to the previous one, 100 µl of a 10% solution of biotinylated R-phycoerythrin in PBS are deposited.

The reaction is left in the dark for 10 minutes, and then a final wash identical to the previous ones is carried out before the detection phase under a microscope.

Example 5

Visualization

The samples deposited onto the gold slide are placed between slide and cover slip and observed with an epifluorescence microscope equipped with a CDD camera under green light and at a magnification of ×1.2. Pictures of the spots are taken and the fluorescence intensities are measured using the Image Pro Plus software.

A) Couplings Using the NHS Pyrrolyl Caproate and the Sulpho-NHS Pyrrolyl Undecanoate Produced in Example 1

These couplings will, here, be demonstrated by fluorescent detection using the affinity couple consisting of biotin and streptavidin (SA). The effectiveness of these couplings will thus be judged through their fluorescence intensity (IF or grey levels).

Four types of spots were produced according to the scheme below:
MR=reaction medium: 50 mM phosphate buffer, pH 7, and 20 mM pyrrole:
IF=10;
A=SA coupled to pyrrole via the NHS pyrrolyl caproate;
IF=200;
BA=SA coupled to pyrrole via the sulpho-NHS pyrrolyl undecanoate:
IF=240;
T=control: SA alone+MR:
IF=80;
with IF=fluorescence intensity.
Black=background noise.

Figure 7:
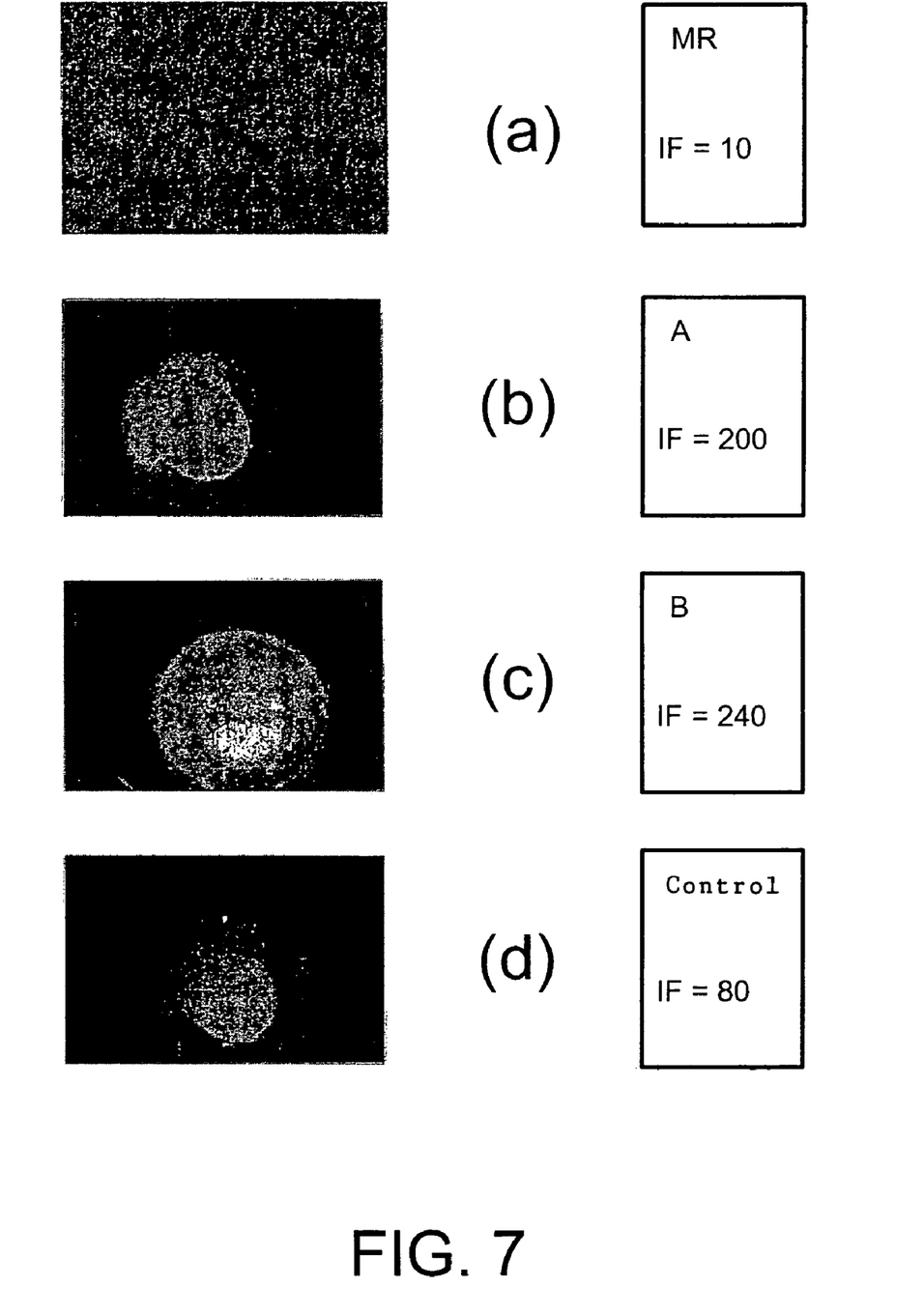

They are represented in this order, respectively, in the attached FIGS. 7a), b), c) and d).

The MR spot controls the non-specific adsorption at the surface of the polypyrrole film. In accordance with our expectations, it exhibits little fluorescence.

The control spot corresponds to the streptavidin not coupled to pyrrole. It is therefore adsorbed onto the polypyrrole. This spot shows a fluorescence intensity that is clearly less than those of the SA-pyrrole samples A and B. This demonstrates that the presence of pyrrole promotes the attachment of streptavidin to the surface of the gold plate.

The A and B spots correspond to streptavidin coupled to polypyrrole via, respectively, the NHS caproate and the sulpho-NHS undecanoate. In comparing the fluorescence intensities of these two spots, it is noticed that the signal obtained is slightly greater when the SA is coupled via the sulpho-NHS pyrrolyl undecanoate than when it is coupled via the NHS pyrrolyl caproate. This difference is very probably due to the length of the chain constituting this NHS; it would make it possible to maintain the accessibility of the sites for the attachment of the biotin.

Overall, it is concluded that this coupling, that gives good results on streptavidin, is possible on other types of proteins.

B) Couplings Using Three Different Maleimides

Five types of spots were produced according to the scheme below:
MR=reaction medium: 50 mM phosphate buffer, pH=7, and 20 mM pyrrole;
T=control: MR+SA alone;
A=MR+SA coupled to pyrrole via the trioxatridecanoyl maleimide;
B=MR+SA coupled to pyrrole via the ethyl maleimide;
C=MR+SA coupled to pyrrole via the hexyl maleimide.

Figure 8:
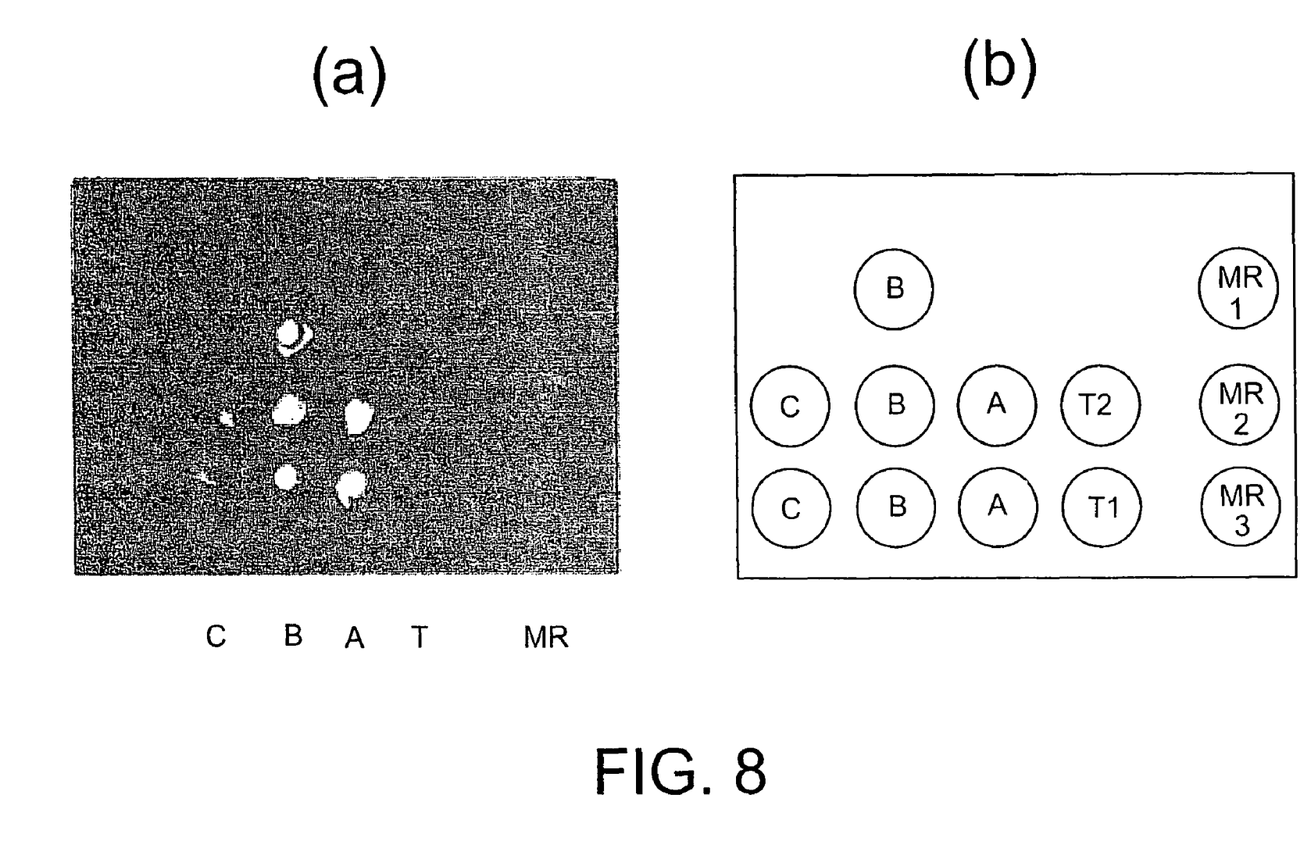

FIGS. 8(a) and (b) illustrate the fluorescence intensity measurements for the various streptavidin-pyrrole conjugates. The spots are deposited according to the scheme of FIG. 8(b). The references in this figure correspond to those indicated above.

The fluorescence intensity measurements taken on these photos are recapitulated in Table 2 below.

The MR1, MR2 and MR3 spots, in accordance with the inventors' expectations, exhibit little fluorescence, which shows the absence of non-specific adsorption.

The controls T1 and T2 corresponding to the SA not coupled to pyrrole, and therefore adsorbed onto the polypyrrole, show a fluorescence that is much less than those of the SA-pyrrole samples.

Thus, the presence of the pyrrole on the molecule promotes, here also, the attachment of the streptavidin.

In comparing the fluorescence intensities for these three spacer arms, it is noted that better fluorescence is obtained for the trioxatridecanoyl arm, followed by the ethyl arm and, finally, the hexyl arm.

TABLE 2

Recapitulation of the light intensities for the various polymers

| Electropolymerization | | Fluorescence intensity |
|---|---|---|
| SA + pyrrole 1 | A1 | 960 |
| | A2 | 1025 |
| SA + pyrrole 2 | B1 | 497 |
| | B2 | 457 |
| | B3 | 437 |
| SA + pyrrole 3 | C1 | 150 |
| | C2 | 200 |

TABLE 2-continued

Recapitulation of the light intensities for the various polymers

| Electropolymerization | | Fluorescence intensity |
|---|---|---|
| SA alone | T1 | 96 |
|  | T2 | 91 |
| MR | MR1 | 10 |
|  | MR2 | 10 |
|  | MR3 | 10 |

As things currently stand in the studies, the inventors are not able to determine with certainty why one arm exhibits a better signal than another. The reply to this question requires further studies and characterizations. The lines of thought could, for example, be the length and/or the more or less hydrophilic nature of the arms, but also the effectiveness of the coupling, etc.

Example 6

Antibodies

A) Coupling of Antibodies with the NHS-Pyrrole

The NHS pyrrolyl caproate is used here, along with three different antibody types:
 i) a rabbit immunoglobulin G,
 ii) an anti-hCG (human Chorionic Gonadotropin) immunoglobulin.

i) Rabbit IgG 10 mg of immunoglobulin G (IgG) are taken up in 333 µl of PBS. The procedure is carried out with an IMR of 40. Thus, 12.5 µl (2.5 nmol) of this solution were mixed with 6.7 µl (100 nmol) of a 15 mM solution of NHS pyrrolyl caproate in DMSO. The reaction is left for 2 h 30 min.

The samples are subsequently purified using Nalgene 30K filters, at 8000 rpm for 20 minutes, and rinsed three times with 100 µl of spotting buffer, a centrifugation of 20 minutes being necessary between each rinse.

Finally, the IgG-pyrroles are recovered in a volume of 50 µl of spotting buffer.

ii) Anti-hCG Immunoglobulin

Two different anti-hCG antibodies (IgG) are available, both derived from mice, HT 13 and FBT 10. The protocol followed is the same for each one of them.

1 nmol of antibody is added to 67 µl of a 15 mM solution of pyrrolyl caproate in DMSO. The mixture is left to act for 2 h 30 min.

The samples are filtered, as previously, using Nalgene filters, and rinsed three times with 100 µl of spotting buffer. Two samples of anti-hCG IgG-pyrrole are recovered in solution in spotting buffer and in a volume of 50 µl.

B) Electrochemical Synthesis of Polypyrrole: Spotting

The copolymerization is the same for the two models under consideration.

Here, it is carried out with 40 µl of a solution containing 20 µl of the IgG-pyrrole solution (whatever it is) and 20 µl of spotting solution (20 mM phosphate buffer, 20 mM pyrrole).

C) Phase Consisting of Detection of the Antibodies Grafted onto the Spots, by Fluorescence In the following two models, the spots are rinsed twice with 1 ml of 10 mM PBS buffer, 1% BSA, 0.05% (w/w) Tween between each step, and all the reactions are carried out at ambient temperature.

i) Rabbit IgG

After the electrochemical synthesis, the spots are rinsed and then blocked with 100 µl of rinsing buffer (10 mM PBS, 1% BSA, 0.05% (w/w) Tween) for 30 minutes. After a second rinse, 100 µl of a solution of biotinylated anti-human or -rabbit IgG antibody, respectively diluted to 1/10 000 and to 1/50 000, are added. The reaction is left for 30 minutes. After further rinsing, 100 µl of a streptavidin R-phycoerythrin solution at 10% in rinsing buffer are added for 10 minutes in the dark. The detection of fluorescence is carried out as above in Example 4.

ii) Anti-hCG Immunoglobulin

The protocol followed is the same as above with regard to the blocking and rinsing steps, 100 µl of a 300 nM solution of hCG in 10 mM PBS buffer, 1% BSA, 0.05% (w/w) Tween are deposited onto the spots. The reaction is left for 30 minutes. Further rinsing is carried out, and then 100 µl of a solution of anti-hCG antibody different from that attached to the plate, and originating from rabbit, diluted to 1/2000, are added. It is left to act for 30 minutes. Further rinsing is carried out, and then 100 µl of a solution of biotinylated anti-rabbit IgG, diluted to 1/10 000, are added.

The reaction is left for 30 minutes. After rinsing, the visualization is carried out as above.

D) Surface Plasmon Resonance (SPR) Experiments with the Antibodies

In order to be able to able to analyse the functionality of the blocks, the inventors employed conditions of a fixed angle of incidence in order to measure the kinetics of variation of the reflectivity as a function of time.

The details of the instrumentation used are given in the document P. Guedon et al., mentioned above.

Figure 9:
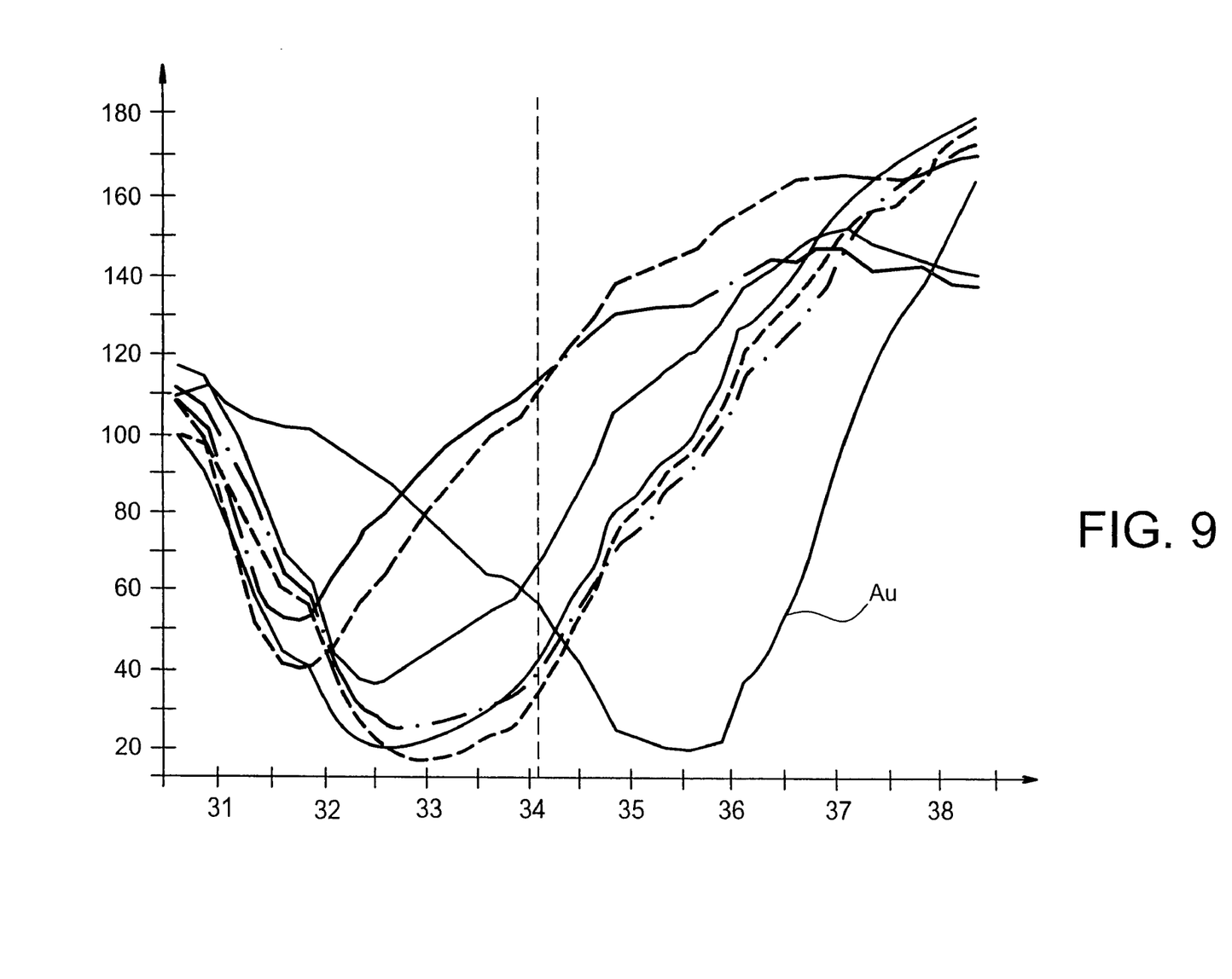
FIG. 9 is a graphic representation of the results of surface plasmon resonance (SPR) assays with antibodies.

FIG. 9 is a graphic representation of the plasmon in buffer obtained.

The inventors thus used conditions of around 34.1°, in order to be in the right flank of the absorption peak of the reflectivity curve.

The protocol was as follows:
 blocking step, solution containing 10 mM PBS, 1% BSA and 0.05% Tween, intended to limit the subsequent non-specific interactions,
 measurement and recording of the reflectivity as a function of the angle of incidence in blocking medium that serves as buffer,
 step with biotinylated anti-rabbit IgG, diluted to 1/100,
 return to blocking in order to measure the difference in level in the same medium before and after antibody uptake,
 step with LCG, diluted to 1/100,
 return to blocking in order to measure the difference in level in the same medium before and after antibody uptake,
 step with anti-hCG IgG derived from rabbit, diluted to 1/2000,
 return to blocking in order to measure the difference in level in the same medium before and after antibody uptake,
 step with the biotinylated anti-rabbit IgG, diluted to 1/100,
 return to blocking in order to measure the difference in level in the same medium before and after antibody uptake,
 step with regeneration buffer, solution containing 0.1 M glycine and hydrochloric acid (pH=2.3),
 return to blocking in order to compare the initial level in blocking during the plasmon and the final level.

This plate is, firstly, visualized with biotinylated anti-rabbit IgGs, then with hCG, anti-hCGs derived from rabbit and, finally, biotinylated anti-rabbit IgGs. The experiment lasts 5 h 20 min.

Figure 10:
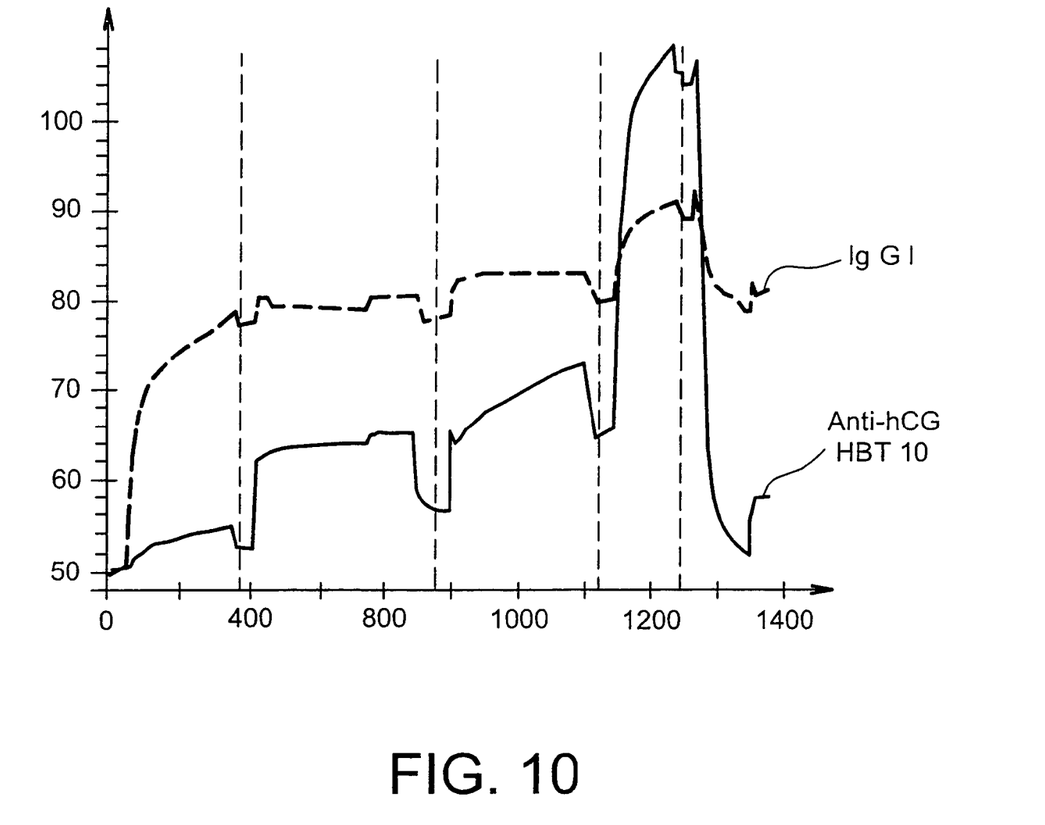
FIG. 10 represents the kinetics of recognition of blocks consisting of rabbit immunoglobulins G (IgG) and of HBT 10 (anti-hCG antibody) attached to a conductive polymer according to the method of the invention.

The attached FIG. 10 is a graphic representation of the kinetics of the deposits on the plate: 2 deposits consisting of rabbit IgG (IgG 1) and of HBT 10 (anti-hCG antibody).

This experiment demonstrates that the stacking of the various proteins takes place as desired. The various plateaus corresponding to the attachment of the injected proteins to the deposit(s) are also noted. The deposit consisting of rabbit IgG takes only anti-rabbit IgGs, and no hCG. The deposit consisting of HBT 10 clearly attaches hCG, this proving that there is no cross-reaction between the two types of rabbit antibody, namely the rabbit IgGs attached to the plate and the anti-hCGs derived from rabbit.

Example 7

Influence of the Polymer Deposit Thickness on the Recognition Capacity of a Protein Grafted onto/into this Polymer An antibody against IgG from rabbit is grafted into the polymer according to the method given in Example 6.

The deposits are produced using the same reaction medium (50 mM sodium phosphate buffer, pH 7, 20 mM pyrrole IgG). The deposits, produced in duplicate for A to F and in triplicate for G, are produced by electrospotting for varying times, thus generating polymers of variable thicknesses. The synthesis charges are measured and the thickness of the polymer can thus be evaluated.

Figure 11:
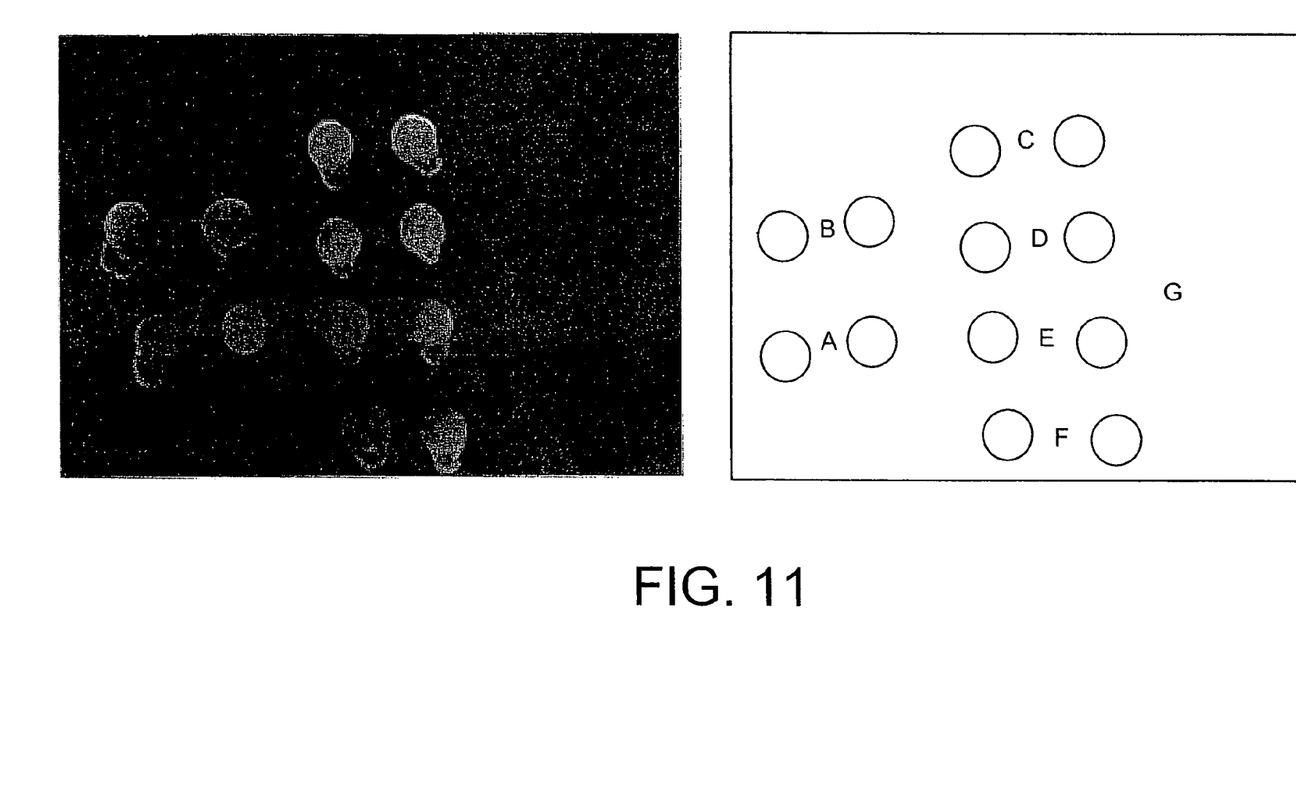
FIG. 11 is a micrograph of fluorescence intensities measured as a function of the thickness of the polypyrrole film, obtained under the operating conditions described in Example 7.

The biochip produced is subsequently treated with biotinylated anti-rabbit IgGs and the recognition is then detected by means of streptavidin-phycoerythrin (see Example 6). The image obtained is given in the attached FIGS. 11(a) and (b) and the quantitative results (Fluorescence Intensities) are given in Table 3 below. FIG. 11(b) is a diagrammatic representation of photograph 11(a), making it possible to demonstrate the deposits.

The results show that, when the polymer is too thick, recognition with the anti-rabbit IgG (large molecule) occurs with difficulty. In the case of thick polymers, an entrapment system like that described by Wolowacz et al., in *Anal. Chem.* 1992, 64, 1541-1545, is obtained. In the case of fluorescence, the optimum thickness is of the order of 10 nm, which corresponds more or less to the diameter of the molecule immobilized. It cannot therefore be simply entrapped in the polymer, which implies a covalent attachment. This same polymer thickness (less than 10 nm) makes it possible, moreover, to optimize the detection by plasmon resonance (P. Guedon et al., *Anal. Chem.* 2000 72, (24), 6003-6009).

TABLE 3

| Blocks | Synthesis time (ms) | Charge (µC) | Charge (µC/mm²) | Thickness (nm) | IF (AU) |
|---|---|---|---|---|---|
| A | 250 | 10 | 25 | 5 | 90 |
| B | 500 | 15 | 37 | 7.2 | 102 |
| C | 1000 | 20 | 50 | 10 | 160 |
| D | 2000 | 37 | 90 | 18 | 140 |
| E | 4000 | 58 | 142 | 28 | 90 |
| F | 8000 | 115 | 287 | 56 | 80 |
| G | 16 000 | 205 | 512 | 102 | 30 |

CONCLUSION

The thickness of the polymer therefore plays a key role in the capacity for attachment, and especially in the capacity for recognition, of hindered proteins. The thicknesses or the charge densities for electropolymerization described in the literature can therefore be compared: Wolowacz et al. propose films that incorporate glucose oxidase; the polymerization densities are of the order of 1.4 mC/mm² (i.e. a film thickness of approximately 280 nm). In this case, the sensor functions since, by virtue of the porosity of the polymer, it allows diffusion of a small analyte, glucose. More recently, Sadik et al., in the abovementioned document, propose an immunosensor on the human serum albumin (HAS) model; the thickness of the polypyrrole film used for entrapment of the protein is a minimum of 350 nm, i.e. a polymerization charge density of 1.5 mC/mm².

No prior art has described or suggested that the thickness of the polymer may have an influence on the biological response of a biosensor. The inventors are therefore the first to provide a method that takes into account this parameter, making it possible, unexpectedly, to solve the abovementioned problems of the prior art.

The invention claimed is:

1. A method for attaching at least one protein to a conductive support, comprising:
    coupling an activated pyrrole monomer directly to a protein to be attached to said conductive support to obtain a first solution of a protein-pyrrole coupling compound,
    mixing the first solution with a second solution comprising a pyrrole not coupled to the protein to obtain an electropolymerization solution,
    electropolymerizing the electropolymerization solution on at least one area of a conductive support, said electropolymerization being carried out with a charge of less than 50 µC/mm² for a synthesis time of less than 1000 ms to produce a copolymer film having a thickness ranging from 5 nm to 10 nm;
    wherein the activated pyrrole is at least one selected from the group consisting of an NHS-pyrrolyl caproate, a sulpho-NHS pyrrolyl undecanoate, 2. The method according to claim 1, wherein the at least one conductive area on which the electropolymerization is carried out is at least one block of a biosensor support.

3. The method according to claim 1, wherein at least two proteins are attached to the pyrrole polymer successively and on two different areas of the conductive support.

4. The method according to claim 1, wherein at least one protein attached to said conductive support is an enzyme.

5. The method according to claim 1, wherein at least one protein attached to said conductive support is an antibody.

6. The method according to claim 1, wherein at least one protein attached to said conductive support is an antigen.

7. The method according to claim 1, wherein at least one protein attached to said conductive support is a hormone.

8. The method according to claim 1, wherein at least one protein attached to said conductive support is a receptor.

9. The method of claim 1 in which said protein is attached to a conductive support which is a monosensor or multisensor or attached to a conductive support used to fabricate a monosensor or multisensor.

10. The method of claim 1 in which said protein is attached to a conductive support which is a biochip or attached to a conductive support used to fabricate a biochip.

11. The method of claim 1 in which said protein is attached to a conductive support which is or forms a part of a surface plasmon resonance device and said electropolymerization produces a copolymer film less than or equal to 10 nm.

12. The method of claim 1 in which said protein is attached to a conductive support which is or forms a part of a device used for fluorescent detection and said electropolymerization produces a copolymer film about the diameter of the immobilized protein.

13. The method of claim 1 in which two or more proteins are electropolymerized to a conductive support which is or forms a part of a biosensor by separately or sequentially performing said coupling, mixing, and electropolymerizing steps with two or more proteins to be attached to said conductive substrate.

14. The method of claim 1, wherein the activated pyrrole monomer is selected from the group consisting of:

15. A method for attaching at least one protein to a conductive support, comprising:

coupling an activated pyrrole monomer directly to a protein to be attached to said conductive support to obtain a first solution of a protein-pyrrole coupling compound, mixing the first solution with a second solution comprising a pyrrole not coupled to the protein to obtain an electropolymerization solution, electropolymerizing the electropolymerization solution on at least one area of a conductive support for a time and under conditions which produce a copolymer film having a thickness ranging from 5 nm to 10 nm;

wherein the activated pyrrole is at least one selected from the group consisting of an NHS-pyrrolyl caproate, a sulpho-NHS pyrrolyl undecanoate, 16. A method for producing a biochip or biosensor comprising:
  attaching at least one protein to a conductive biosensor support, comprising:
    coupling an activated pyrrole monomer directly to a protein to be attached to said conductive support to obtain a first solution of a protein-pyrrole coupling compound,
    mixing the first solution with a second solution comprising a pyrrole not coupled to the protein to obtain an electropolymerization solution,
    electropolymerizing the electropolymerization solution on at least one area of a conductive biosensor support for a time and under conditions which produce a copolymer film having a thickness ranging from 5 nm to 10 nm;
  wherein the activated pyrrole is at least one selected from the group consisting of an NHS-pyrrolyl caproate, a sulpho-NHS pyrrolyl undecanoate, 17. The method of claim 16 which produces a plasmon resonance sensor.

* * * * *